US011589781B2

(12) United States Patent
Motamedi et al.

(10) Patent No.: US 11,589,781 B2
(45) Date of Patent: Feb. 28, 2023

(54) ASSESSING DISEASES BY ANALYZING GAIT MEASUREMENTS

(71) Applicant: GEORGETOWN UNIVERSITY, Washington, DC (US)

(72) Inventors: Gholam Motamedi, Washington, DC (US); Ophir Frieder, Chevy Chase, MD (US); Cristopher Flagg, Annandale, VA (US); Jian-Young Wu, Gaithersburg, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 16/889,642

(22) Filed: Jun. 1, 2020

(65) Prior Publication Data

US 2020/0375501 A1 Dec. 3, 2020

Related U.S. Application Data

(60) Provisional application No. 62/910,853, filed on Oct. 4, 2019, provisional application No. 62/855,664, filed on May 31, 2019.

(51) Int. Cl.
*A61B 5/11* (2006.01)
*A61B 5/00* (2006.01)
*G06F 40/205* (2020.01)

(52) U.S. Cl.
CPC ............ *A61B 5/112* (2013.01); *A61B 5/4842* (2013.01); *A61B 5/7267* (2013.01);
(Continued)

(58) Field of Classification Search
CPC ..... A61B 5/112; A61B 5/4842; A61B 5/7267; A61B 5/7264; A61B 5/7275; A61B 5/742;
(Continued)

(56) References Cited

U.S. PATENT DOCUMENTS

2004/0228503 A1 11/2004 Cutler
2009/0030350 A1 1/2009 Fang et al.
(Continued)

FOREIGN PATENT DOCUMENTS

EP 3451236 A1 3/2019
WO 2017181093 A1 10/2017

OTHER PUBLICATIONS

Zhao, LSTM for diagnosis of neurodegenerative diseases using gait data, Apr. 10, 2018, Proc. SPIE 10615, Ninth International Conference on Graphic and Image Processing (ICGIP 2017), 106155B (Year: 2018).*

(Continued)

*Primary Examiner* — Patrick Fernandes
(74) *Attorney, Agent, or Firm* — Blank Rome LLP

(57) ABSTRACT

A gait analysis system, which includes a neural network with a recurrent neural network layer and a fully connected layer, that receives sensor data indicative of an individual's gait and outputs an assessment regarding the individual's health. The neural network is trained using training data indicative of abnormal gaits and normal gaits. To analyze the training data and the sensor data, the recurrent neural network layer parses each piece of data into a series of windows and analyzes each window in series to generate a context vector characterizing each window and the previously analyzed windows. The fully connected layer, having been trained to differentiate between normal gaits and abnormal gaits based on context vectors characterizing the training data, is used to generate a final assessment characterizing the user gate as normal or abnormal using one or more of the context vectors characterizing the sensor data.

18 Claims, 13 Drawing Sheets

(52) U.S. Cl.
CPC ............ *A61B 5/7275* (2013.01); *A61B 5/742* (2013.01); *G06F 40/205* (2020.01); *A61B 2562/0219* (2013.01); *A61B 2562/0247* (2013.01)

(58) Field of Classification Search
CPC .... A61B 2562/0219; A61B 2562/0247; A61B 2503/10; A61B 5/0022; A61B 5/1112; A61B 2505/09; A61B 5/4082; G06N 3/02; G06N 7/046; G06N 20/00; G06N 20/10; Y10S 128/925; G06F 40/205; G16H 20/30
See application file for complete search history.

(56) References Cited

U.S. PATENT DOCUMENTS

| | | | |
|---|---|---|---|
| 2014/0156215 | A1 | 6/2014 | Eastman et al. |
| 2016/0007885 | A1 | 1/2016 | Basta et al. |
| 2017/0143240 | A1 | 5/2017 | Stone et al. |
| 2017/0258390 | A1 | 9/2017 | Howard |
| 2019/0283247 | A1* | 9/2019 | Chang .................... A61B 5/112 |
| 2019/0329118 | A1 | 10/2019 | Balakrishnan et al. |
| 2021/0007603 | A1* | 1/2021 | Huddleston ............ G06V 10/25 |
| 2021/0117815 | A1* | 4/2021 | Creed ..................... G06F 17/16 |

OTHER PUBLICATIONS

Zou et al., "Deep Learning Based Gait Recognition Using Smartphones in the Wild"; Journal of Latex Class Files, vol. X, No. X, Jun. 2018 [online], pp. 1-13; published Jun. 2018 [retrieved on Aug. 19, 2020]. Retrieved from the Internet <URL:https://arxiv.org/abs/1811,00338> entire document, especially pp. 1-13, entire document (especially p. 2, col. 1, para 2, p. 5, col. 1, para 2, p. 6, col. 2, para 3).

International Search Report; International Application No. PCT/IB20/55183; International Filing Date Jun. 1, 2020; 2 pages.

* cited by examiner

ASSESSING DISEASES BY ANALYZING GAIT MEASUREMENTS

CROSS-REFERENCE TO RELATED APPLICATIONS

This application claims priority to U.S. Prov. Pat. Appl. No. 62/855,664, filed May 31, 2019, and U.S. Prov. Pat. Appl. No. 62/910,853, filed Oct. 4, 2019, each of which are hereby incorporated by reference in their entirety.

FEDERAL FUNDING

None

BACKGROUND

Human gait is controlled by a complex set of interactions between multiple organ systems. Keeping balance while standing on two feet with relatively small surface area requires very complex and delicate interactions between the musculoskeletal system on the one hand and the peripheral nervous system (PNS) and the central nervous system (CNS) on the other. This task becomes even more complicated considering that, while walking, the whole body stands only on one foot while the other foot is lifted and has to be put back on the ground in synchrony with the other foot. Mechanically, this process requires proper muscle tone and strength, proper bone and joint function, and very fast communications between these end organs and the CNS.

The organ systems involved in coordinating this complex task include muscles with specialized microscopic organelles, including golgi tendon organs that sense tension in the tendons and spindles that sense the speed of muscle stretch. This sensory information is transferred, along with the proprioceptive data carried through the PNS, to different parts of the CNS for a real-time analysis and correction to keep the body in a stable position while moving at different speeds and directions. Keeping the body in a stable position requires the integrity of the PNS to transfer the peripheral input to the CNS where complex back-and-forth interactions between the thalamus, basal ganglia, the sensory-motor cortex, and the cerebellum provides a real-time guidance back to the musculoskeletal system.

Any deterioration in the structures involved in this process may result in gait abnormality. As a result, gait abnormalities may present in many different ways. For example, patients with Parkinson's disease or parkinsonism (a set of similar neurodegenerative disorders) are increasingly at risk of falling because a variety of mechanisms involved in walking are affected. Patients with Parkinson's disease or parkinsonism can experience freezing of the upper body during a walk, causing them to be thrown forward and, given their slowed postural reflexes, causing many to fall. To compensate, patients with Parkinson's disease or parkinsonism develop rapid, small, shuffling steps and a tendency to run (festination). As the disease progresses, movements are further impaired leading to stiffness and episodic immobility known as "freezing of gait." Peripheral neuropathy can interfere with signal transduction (in particular deep positional sensation carried by thick myelinated nerves) to the CNS. Therefore, patients with severe peripheral neuropathy may not feel their position in space fast enough to correct their position and fall during walking. Patients with certain muscle disorders (such as muscular dystrophy) may lack sufficient strength in the pelvic girdle muscles and may turn her or his pelvis to drag the patient's foot forward (called "waddling gait") to compensate. Patients with cerebellar disorders (e.g., stroke, tumor, and degenerative disorders) typically develop wide-based gait to keep balance. Even an individual's mood—and, by extension, depressive illnesses—may affect an individual's gait. Clinically depressed patients have been found to have demonstrated a smaller push-off force in the posterior and downward directions.

Injuries to the body can also affect an individual's gait. Anyone who has suffered a fall, pulled a hamstring, or injured a leg muscle will often notice a difference in their gait. Additionally, head trauma that will eventually lead to a concussion may also affect an individual's gait before the concussion is developed.

Because certain diseases affect an individual's gait, gait analysis may then be used to identify and assess those diseases. In fact, because certain diseases may be detectable by analyzing an individual's gait before those diseases are detectable by other means, gait analysis may provide an effective diagnostic tool that provides early and effective identification of diseases. Certain injuries, such as head trauma that will eventually cause a concussion, may also be detectable by analyzing an individual's gait before the concussion develops and is detectable by other means. Additionally, because a progressive disease's effect on an individual's gait may vary at different stages of the progressive disease, analysis of the individual's gait may be used to assess the progress of the progressive disease. Conversely, because an individual's gait may progress towards normal as the individual recovers, the analysis of the individual's gait may be used to assess the progress of the individual's recovery.

As described above, there is a need for systems that detect and assess diseases and injuries by analyzing gait measurements. Prior art methods exist for identifying diseases by analyzing gait patterns. However, those existing gait analysis methods determine a patient's gait characteristics (e.g., strike distance, foot lift, foot pressure, etc.) over a number of steps and identify abnormal gait characteristics by analyzing the average gait characteristics from the entire data set collected from the patient. However, degeneration of a patient's gait is a gradual progression that results in only a portion of the gait suffering from abnormalities. Freezing of gait, for example, is episodic and occurs at random intervals. Therefore, gait degeneration may not be detectable by analyzing an entire data set of a patient's gait characteristics as done by prior art gait analysis methods.

Accordingly, there is a need for an improved system that identifies abnormal gait measurements (including gradual, episodic, and/or random abnormalities) and detects and assesses diseases and injuries by analyzing those gait measurements.

SUMMARY

To overcome those and other disadvantages in the prior art, a gait analysis system is provided. The gait analysis system, which includes a neural network with a recurrent neural network layer and a fully connected layer, receives sensor data indicative of an individual's gait and outputs an assessment regarding the individual's health. The neural network is trained using training data indicative of abnormal gaits and normal gaits. To analyze the training data and the sensor data, the recurrent neural network layer parses each piece of data into a series of windows and analyzes each window in series to generate a context vector characterizing each window and the previously analyzed windows. The fully connected layer, having been trained to differentiate between normal gaits and abnormal gaits based on context vectors characterizing the training data, is used to generate a final assessment characterizing the user gate as normal or abnormal using one or more of the context vectors characterizing the sensor data.

The neural network may be trained to distinguish between user gates indicative of a plurality of diseases. The neural network may also be trained to monitor user gaits overtime as they are affected by a progressive disease or as a user recovers. By analyzing gait data from a user at two different time periods, the neural network may be trained to identify whether the user suffered an injury between the two time periods.

The recurrent neural network layer may be bidirectional. The neural network may further include an attention layer that weights each window based on its relative importance. The fully connected layer may be a single layer neural network.

The gait analysis system may use multiple types of sensor data and training data (e.g., acceleration data, pressure or force data, sound recordings, spectrograms of sound recordings, video recordings, etc.). The neural network may be trained in parallel such that the recurrent neural network layer generates the same context vector to characterize the same gait regardless of the type of sensor data.

BRIEF DESCRIPTION OF THE DRAWINGS

Aspects of exemplary embodiments may be better understood with reference to the accompanying drawings. The components in the drawings are not necessarily to scale, emphasis instead being placed upon illustrating the principles of exemplary embodiments.

DETAILED DESCRIPTION

Figure 1:
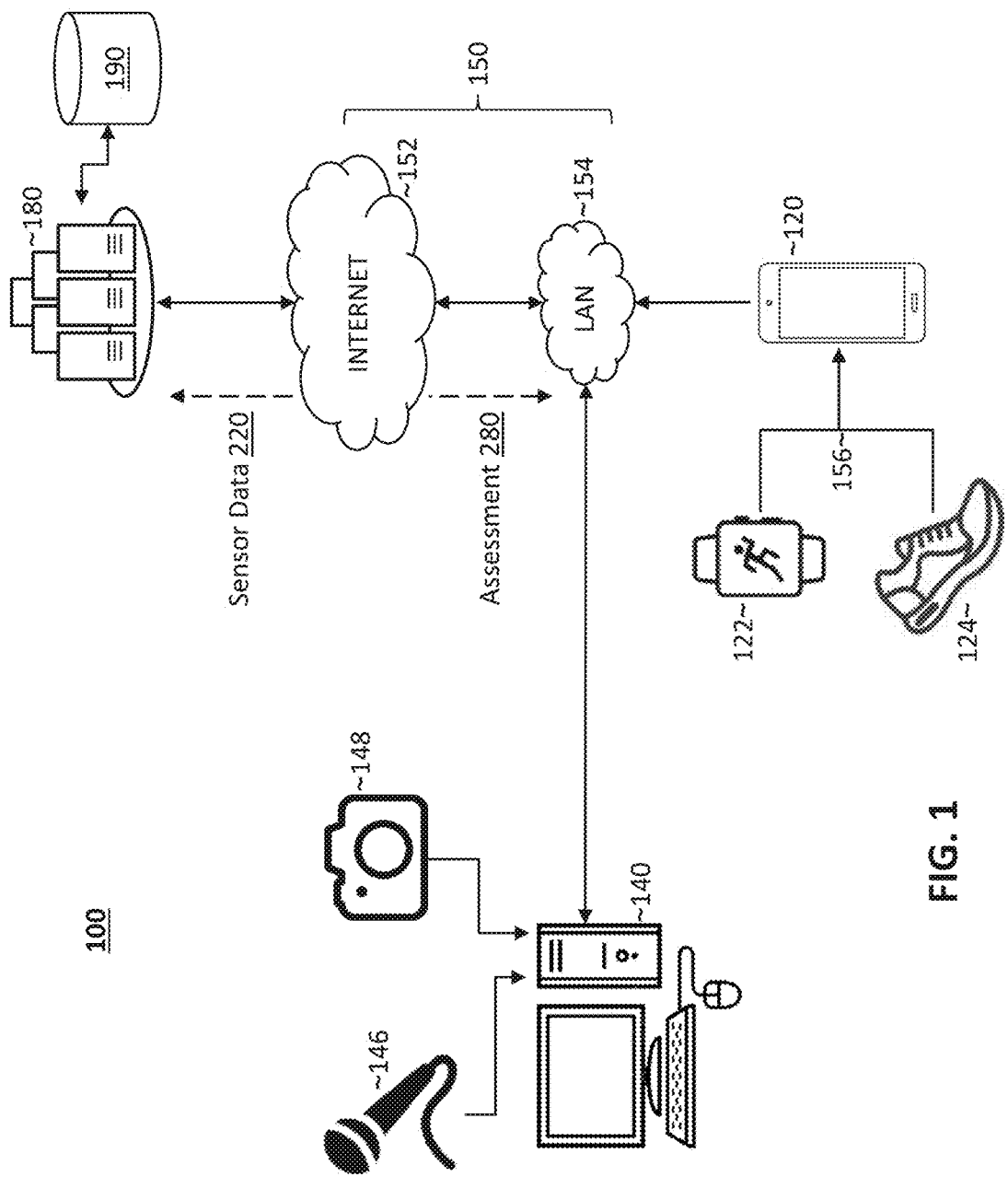
FIG. 1 is a schematic diagram of an architecture 100 of a gait analysis system 200 according to an exemplary embodiment of the present invention.

Reference to the drawings illustrating various views of exemplary embodiments of the present invention is now made. In the drawings and the description of the drawings herein, certain terminology is used for convenience only and is not to be taken as limiting the embodiments of the present invention. Furthermore, in the drawings and the description below, like numerals indicate like elements throughout.

FIG. 1 is a diagram of an architecture 100 of a gait analysis system 200 according to an exemplary embodiment of the present invention.

As shown in FIG. 1, the architecture 100 includes a server 180 that receives sensor data 220 indicative of an individual's gait and outputs an assessment 280 regarding the individual's health. The sensor data 220 may be received via one or more networks 150. The networks 150 may include any combination of the Internet 152, cellular networks, wide area networks (WAN), local area networks (LAN) 154, etc. Communication via the networks 150 may be realized by wired and/or wireless connections.

As described in detail below with reference to FIG. 2, sensor data 220 may be captured by a portable electronic device 120 (e.g., a smartphone), a wearable electronic device 122 (e.g., an activity tracker), or sensor-enabled shoes 124. The wearable electronic device 122 or sensor-enabled shoes 124 may communicate with the portable electronic device 120 via direct, short range, wireless communication signals 156 (e.g., Bluetooth). The portable electronic device 120 may transmit sensor data 220 captured by the wearable electronic device 122 or the sensor-enabled shoes 124 to the server 180 via the network(s) 150.

Additionally or alternatively, sensor data 220 may be captured by a microphone 146 or a video camera 148. Sensor data 220 captured by the microphone 146 or video camera 148 may be transmitted to the server 180 by a remote computer 140 via the network(s) 150. The assessment 280 may be output by the server 180 to the remote computer 140 via the network(s) 150.

The server 180 may be any suitable computing device including, for example, an application server or a web server. The server 180 includes non-transitory computer-readable storage media, such as a hard disk or solid-state memory, and at least one hardware computer processor. In addition to internal memory, the server 180 may store data on external (non-transitory) storage media 190, which may be accessed via a wired connection, via a local area network, etc.

The remote computer 140 may be any suitable computing device, such as a desktop or notebook personal computer, configured to output sensor data 220 to the server 180 via the network(s) 150 and receive and display the assessment 280 via a graphical user interface. The remote computer 140 includes non-transitory computer-readable storage media, such as a hard disk or solid-state memory, and at least one hardware computer processor.

The portable electronic device 120 may be any suitable portable computing device including, for example, a smartphone, a tablet computer, a personal digital assistant, etc.

The portable electronic device 120 may include a 3-axis accelerometer that measures acceleration in three axes (as described, for example, in U.S. Pat. Pub. No. 2014/0156215 to Eastman, et al.). The portable electronic device 120 may also include a gyroscope that can be used to determine the orientation of the portable electronic device 120 relative to the ground. The accelerometer and the gyroscope (collectively referred to as an inertial measurement unit) may be used by the portable electronic device 120 to measure the acceleration of the portable electronic device 120 relative to the ground in three dimensions. The portable electronic device 120 may also include a microphone that records sound and a camera that records video.

The wearable electronic device 122 may be any suitable wearable computing device including, for example, a fitness tracker, an activity tracker, a smart watch, etc. The wearable electronic device 122 may be configured to be worn by a user, for example, around a wrist, an arm, an ankle, etc. Similar to the portable electronic device 120, the wearable electronic device 122 may include an accelerometer and a gyroscope may be used to determine the acceleration of the wearable electronic device 122 in three dimensions (as described, for example, in U.S. Pat. Pub. No. 2019/0329118 to Balakrishnan, et al.).

The sensor-enabled shoes 124 may be any footwear configured to measure physical parameters as the user walks or runs. The sensor-enabled shoes 124 may be equipped with accelerometers and/or force sensors (as described, for example, in U.S. Pat. Pub. No. 2019/0329118 to Balakrishnan, et al.). The accelerometers may be used to determine the acceleration of each sensor-enabled shoe 124. Additionally or alternatively, the force sensors may be used to determine force applied by each foot.

Figure 2:
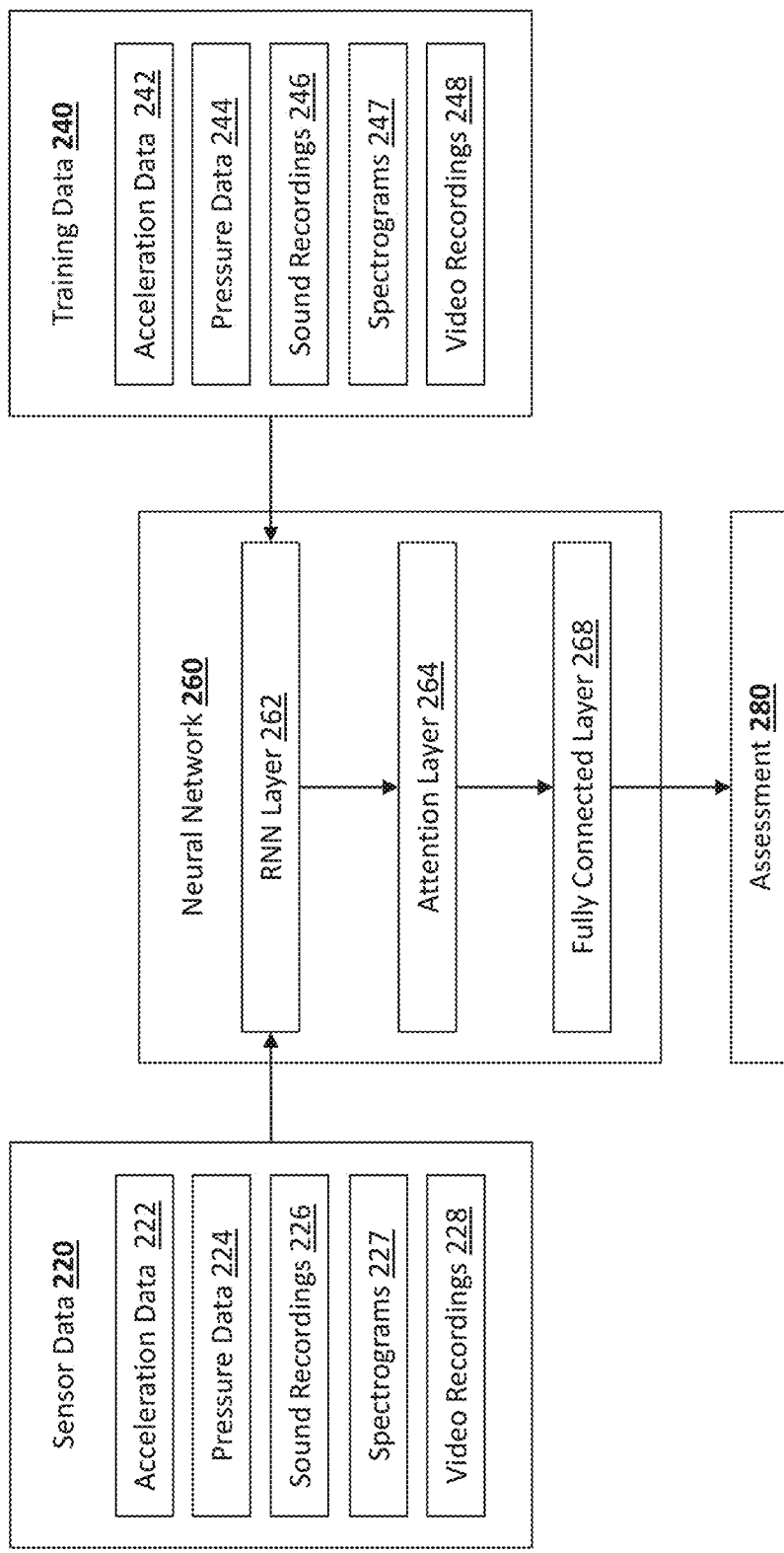
FIG. 2 is a block diagram of the gait analysis system 200 according to an exemplary embodiment of the present invention.

FIG. 2 is a block diagram of the gait analysis system 200 according to an exemplary embodiment of the present invention.

As shown in FIG. 2, the gait analysis system 200 includes a neural network 260 that receives sensor data 220 and training data 240 and determines and outputs an assessment 280 in response to the sensor data 220. Both the sensor data 220 and the training data 240 may include acceleration data 222 or 242, pressure data 224 or 244, sound recordings 226 or 246, spectrograms 227 or 247, and/or video recordings 228 or 248. The neural network 260 includes a recurrent neural network (RNN) layer 262 and a fully connected layer 268. In a preferred embodiment, the neural network 260 also includes an attention layer 264. As those skilled in the art will recognize, other neural network configurations (e.g., convolutional neural networks (CNN) and transformers) can likewise be used.

The acceleration data 222 (or 242) may be any data indicative of the acceleration of a device carried by a user (e.g., in three axes relative to the ground) over time. The acceleration data 222 (or 242) may be captured, for example, by the portable electronic device 120 or the wearable electronic device 122. In those instances, the acceleration data 222 (or 242) may be indicative of the acceleration of the portable electronic device 120 or the wearable electronic device 122.

The pressure data 224 (or 244) may be any data indicative of the force or pressure applied by each foot of a user over time. The pressure data 224 (or 244) may be captured, for example, by sensor-enabled shoes 124.

The sound recordings 226 (or 246) may be any data indicative of the sound waves created by a user while walking or running over time. The sound recordings 226 (or 246) may be captured, for example, by the portable electronic device 120 or the microphone 146.

The spectrograms 227 (or 247) may be any visual representation of the spectrum of frequencies of the audio signal from the sound recordings 226 (or 246) as the audio signal varies with time.

The video recordings 228 (or 248) may be any image data indicative of a user walking or running over time. The video recordings 228 (or 248) may be captured, for example, by the portable electronic device 120 or the video camera 148.

The training data 240 and the sensor data 220 could theoretically be stored locally, for example by the remote computer 140, if the remote computer 140 was provided with a data storage capability. The remote computer 140 could also theoretically train and execute the neural network 260 if the remote computer 140 was provided with sufficient computing power and/or time. (Alternatively, the sensor data 220 could theoretically be provided directly to the server 180 without the use of any of the network(s) 150.) As a practical matter, however, the server 180 will be required to train and execute the neural network 260, using training data 240 stored in the storage media 190, having been provided with sensor data 220 via the network(s) 150.

Figure 3:
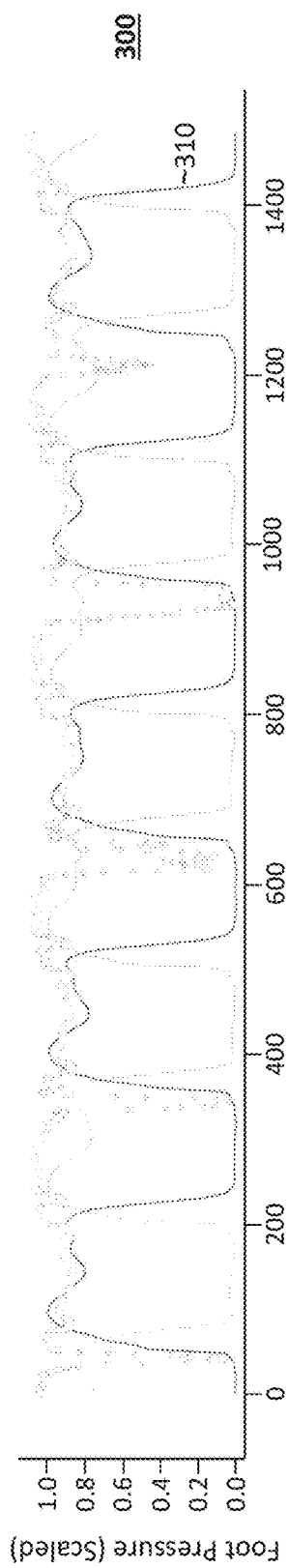
FIG. 3 is a graph of exemplary pressure data.
Figure 4:
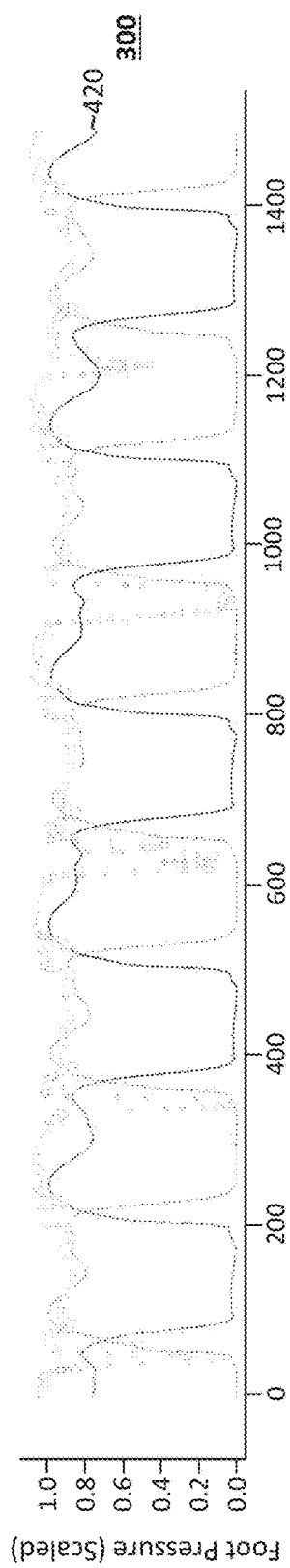
FIG. 4 is another graph of the exemplary pressure data shown in FIG. 3.
Figure 5:
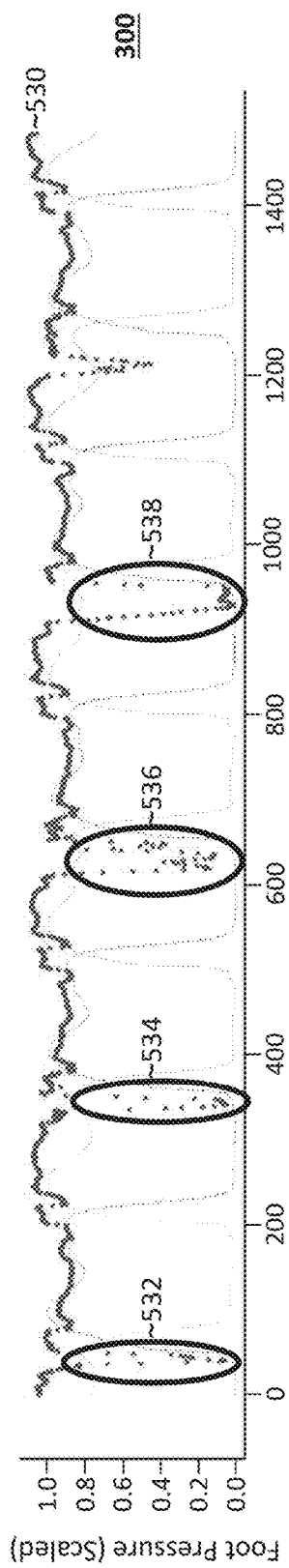
FIG. 5 is another graph of the exemplary pressure data shown in FIG. 3.

FIGS. 3-5 are a graph 300 of exemplary pressure data 224 or 244. As shown in FIG. 3, the graph 300 includes left foot pressure data 310 that have been normalized within a ten second window to range from 0 to 1. As shown in FIG. 4, the graph 300 also includes right foot pressure data 420 that have been similarly normalized within a ten second window to range from 0 to 1. In each instance, a window is passed over the pressure data 224 or 244 and a ten second moving average is computed and used to normalize the streaming data. Any pressure data 244 that exceeds the [0,1] bounds may be clipped to the maximum or minimum value. As described in detail below, the neural network 260 uses the left foot pressure data 310 and the right foot pressure data 420 to generate assessments 280 of the "normality" of the user gait. In the process, the neural network 260 parses the sensor data 220 into sensor data windows. Meanwhile, the neural network 260 may generate gait window assessments 530 indicative of the "normality" of the user gait during each sensor data window. The gait window assessments 530 determined by the neural network 260 are shown in FIG. 5, including areas 532, 534, 536, and 538, which are discussed below.

Figure 6:
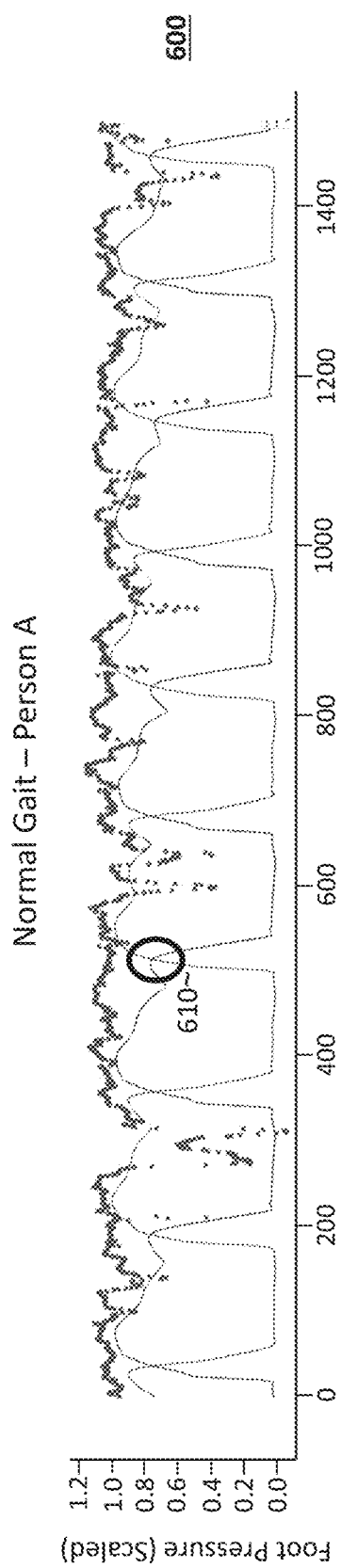
FIG. 6 is a graph of exemplary training data of a first individual with a normal gait.
Figure 7:
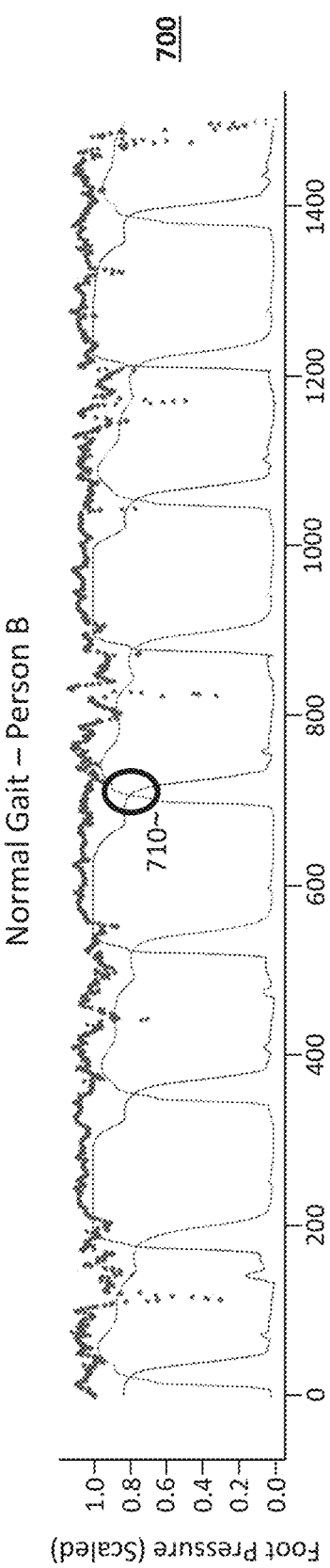
FIG. 7 is a graph of exemplary training data of a second individual with a normal gait.
Figure 8:
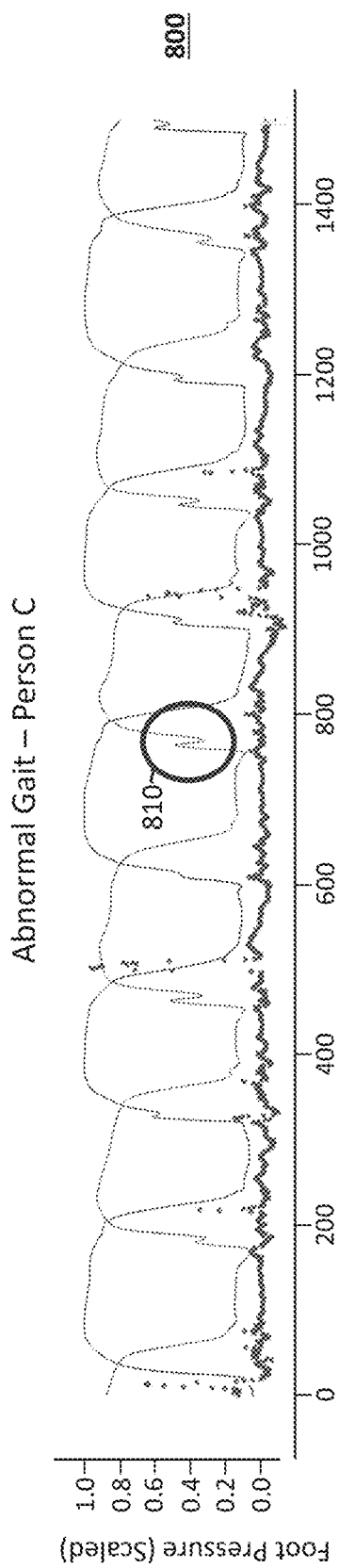
FIG. 8 is a graph of exemplary training data of a third individual with an abnormal gait.
Figure 9:
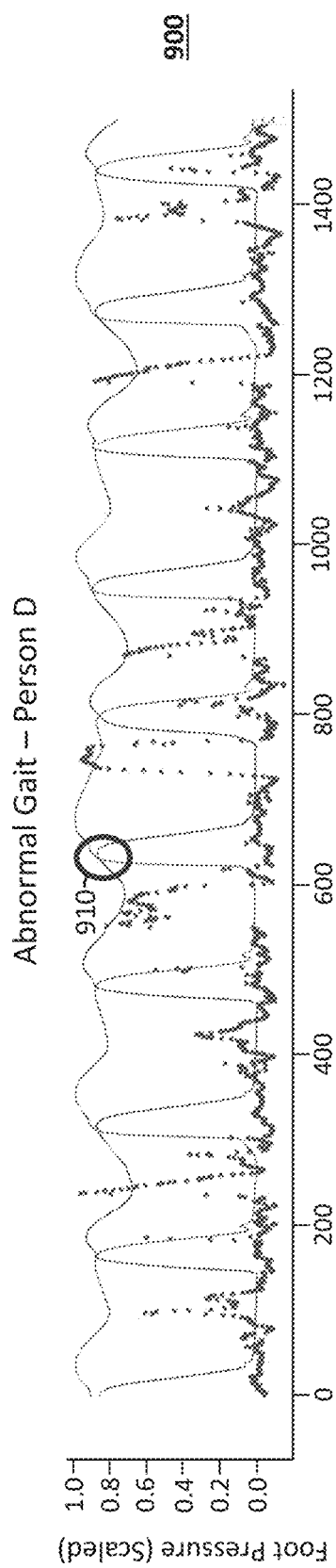
FIG. 9 is a graph of exemplary pressure data of a fourth individual with an abnormal gait.

Using training data 240 that include both individuals with diseases that affect gait and individuals with normal gaits, the neural network 260 can be trained to identify diseases by analyzing sensor data 220. FIG. 6 is a graph 600 of exemplary training data 240 (in this instance, pressure data 244) of a first individual with a normal gait. FIG. 7 is a graph 700 of exemplary pressure data 244 of a second individual with a normal gait. No two gaits are exactly the same. However, as shown in area 610 of FIG. 6 and area 710 of FIG. 7, individuals with normal gaits show similar gait features. FIG. 8 is a graph 800 of exemplary pressure data 244 of a third individual with an abnormal gait. FIG. 9 is a graph 900 of exemplary pressure data 244 of a fourth individual with an abnormal gait. As shown in FIGS. 8 and 9, abnormal gaits differ both in progression of disease as well normal variance. Additionally, abnormal features—for example, shown in area 810 of FIG. 8 and area 910 of FIG. 9—are not present in the pressure data 244 of individuals with normal gaits. Patterns that appear in the training data 240 can be used to identify normal and abnormal gait patterns in the sensor data

220. While pressure data 244 is shown in FIGS. 6-9, the neural network 260 can be similarly trained using other kinds of training data 240.

Figure 10:
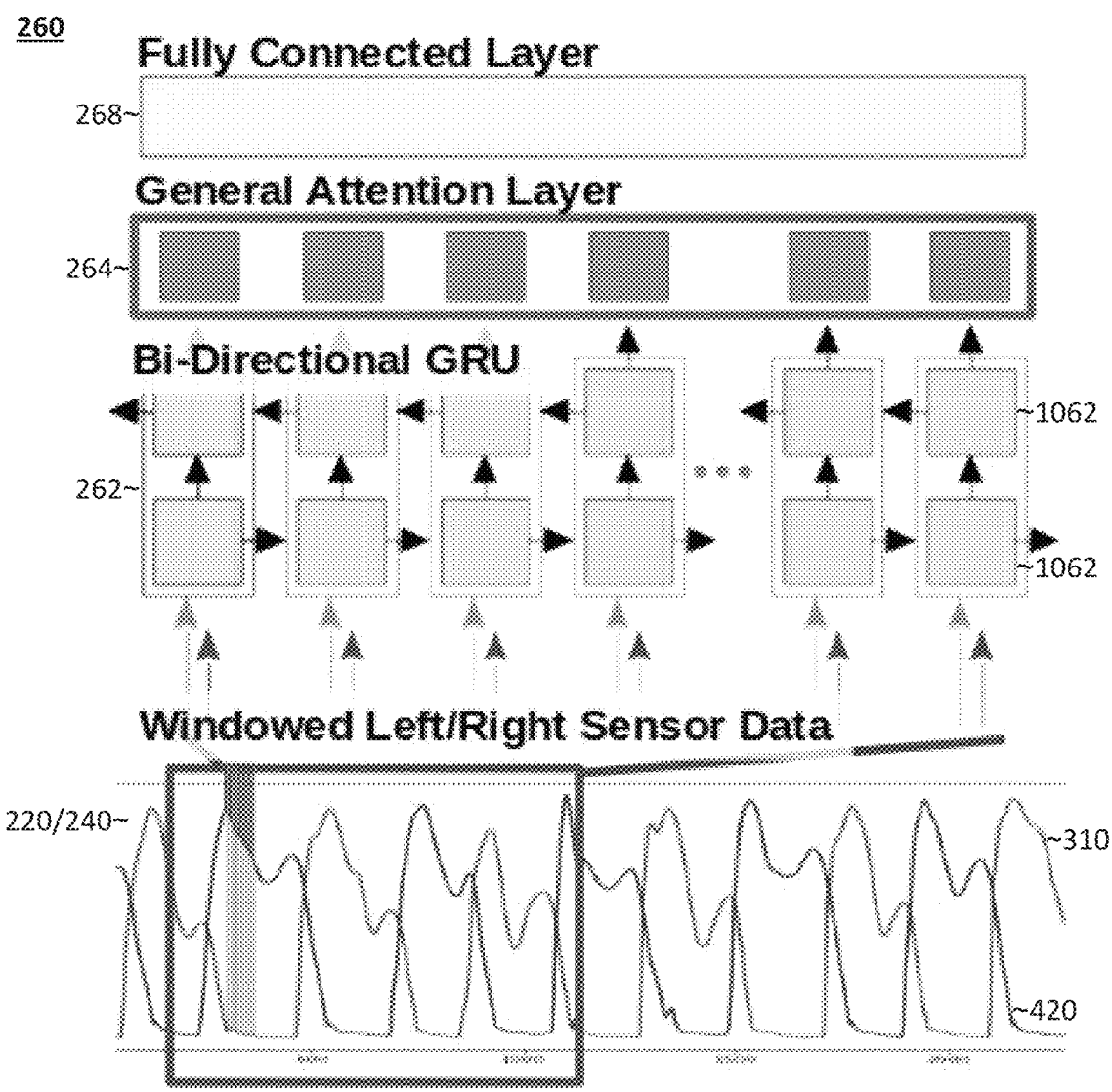
FIG. 10 is a diagram of a neural network according to an exemplary embodiment of the present invention.

FIG. 10 is a diagram of the neural network 260 according to an exemplary embodiment of the present invention.

As shown in FIG. 10, the training data 240 or the sensor data 220 is provided to the recurrent neural network layer 262. Samples may be grouped into a window and passed to the recurrent neural network layer 262 in series. For example, samples may be grouped into a 1-second window (comprising 30 left foot data points and 30 right foot data points), as preliminary studies have shown that a 1-second window provides optimal results with these gait analysis methods. A sliding window may be used by the recurrent neural network layer 262. However, other windowing methods (e.g., discrete windows) may also be used. A "recurrent neural network layer" is a class of artificial neural networks that takes data of a streaming, sequential, or series nature and provides an output that characterizes the sequence or series. The recurrent neural network begins by reading an input vector and generating an output vector. For all subsequent input vectors provided to the recurrent neural network, the network combines the previous recurrent network output vector and the new input vector to create a new output vector. This process is repeated for all of the input data to create a final characterization of the input stream. By providing the recurrent neural network with multiple sequential or series data points, the recurrent neural network is able to capture both information about individual data points as well as information about the relationships between data points. The recurrent neural network layer 262 shown in FIG. 10 is depicted as a bidirectional recurrent neural network with thirty recurrent neural network nodes 1062 in either direction. In practice, the recurrent neural network 1062 may include a single recurrent neural network node 1062 or a set of multiple recurrent neural network nodes 1062 reading the sensor data 220 or training data 240.

Figure 11:
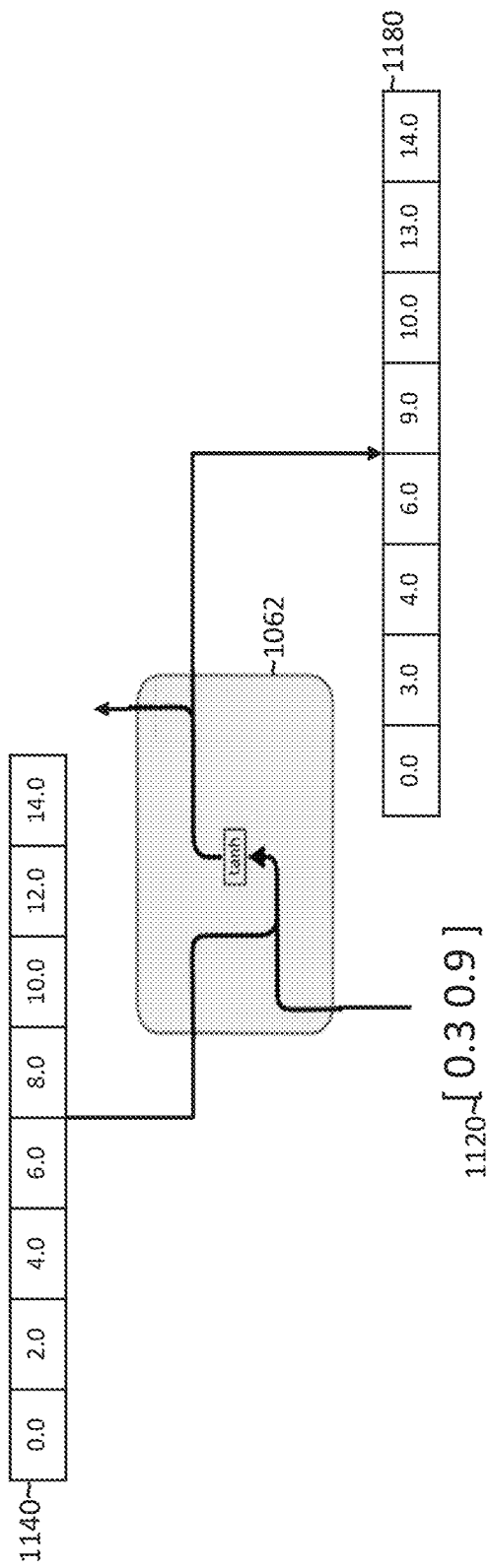
FIG. 11 is a diagram of a recurrent neural network layer according to an exemplary embodiment of the present invention.

FIG. 11 is a diagram of a recurrent neural network node 1062 of the recurrent neural network layer 262 according to an exemplary embodiment of the present invention.

As each new data point 1120 is received, the recurrent neural network layer 262 creates a context vector 1180 describing the new data point 1120 and the previously determined context vector 1140. As described above, each new data point 1120 may be a sample over time from the sensor data 220 or the training data 240 (in the case of pressure data 224 or 244, for example, a 1-second window comprising 30 left foot data points and 30 right foot data points). The context vector 1180 is a series of numbers that are meaningful only to the neural network 260. However, each context vector 1180 represents a non-human readable intermediate assessment of the normality of the gait of the user for the window, determined based on the new data point 1120 for the window and the previously analyzed data points.

The recurrent neural network layer 262 may be a bidirectional recurrent neural network that creates a first context vector 1180 from a forward pass and second context vector 1180 from a backwards pass. Therefore, the recurrent neural network layer 262 will generate a first context vector 1180 characterizing the new data point 1120 and the sensor data 220 (or the training data 240) that came before the new data point 1120 and a second context vector 1180 characterizing the new data point 1120 and the sensor data 220 (or the training data 240) that came after the new data point 1120. In the preferred embodiment shown in FIG. 11, the recurrent neural network layer 262 is a gated recurrent unit (GRU), a variant of the Long Short Term Memory (LSTM) recurrent neural network (RNN) structure. Internally, the GRU uses an update and reset gate to determine which information should be passed to output. These gates determine how much information from previous data should be saved as well as how the saved data are combined with the incoming data to produce the output. While a GRU is preferred, the recurrent neural network layer 262 may be any recurrent neural network. Meanwhile, to analyze spectrograms 227 and 247, the neural network need not be recurrent.

Referring back to FIG. 10, the context vectors 1180 are provided to the attention layer 264. Not all portions of an individual's gait pattern provide the same amount of information about the normality of that individual's gait. Therefore, different data points in the sensor data 220 have different predictive value for determining whether an individual has an abnormal gait pattern. Accordingly, the attention layer 264 identifies the weight of each data point in the training data 240 and applies those weights to each data point in the sensor data 220.

Figure 12:
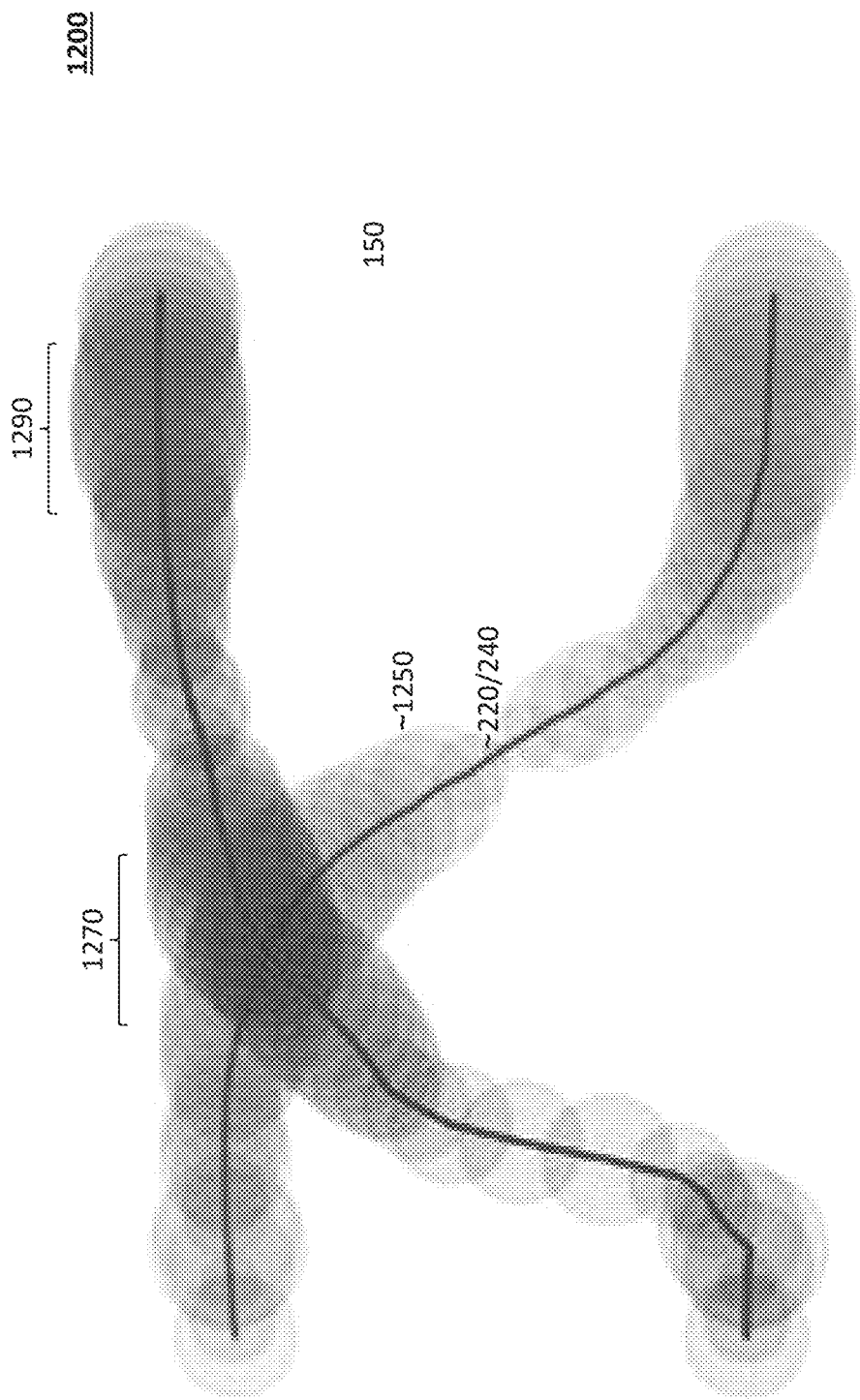
FIG. 12 is a graph illustrating exemplary weights applied to each data point in sensor data or training data 240.

FIG. 12 is a graph 1200 illustrating weights 1250 applied to each data point in the sensor data 220 or the training data 240, where the radius of each circle denotes the amount of attention to be paid to that point in the sensor data 220 or the training data 240. As shown in FIG. 12, the attention layer 264 may place greater weight on the data points during the crossover period 1270 (when the two foot pressures are equal and the balance shifts from one foot to the other) and during the time period 1290 when all of the pressure is on one foot (while the other has been lifted and is being swung forward).

The attention layer 264 is a fully connected layer that, having been trained using the training data 240, takes each context vector 1180 and provides a weight 1250 that represents the importance of that data point. Each context vector 1180 is adjusted by its weight 1250, combined with the other weighted context vectors 1180, and normalized.

Referring back to FIG. 10, the weighted, normalized, and combined context vectors 1180 are provided to the fully connected layer 268.

As one of ordinary skill in the art would recognize, artificial neural networks are computing systems (vaguely inspired by the biological neural networks) that "learn" to perform tasks by considering examples, generally without being programmed with task-specific rules. In this instance, the fully connected layer 268 is trained to recognize normal and abnormal gaits in the sensor data 220 by considering examples of normal and abnormal gaits in the training data 240.

Specifically, the fully connected layer 268 analyzes the context vectors 1180 (generated by the recurrent neural network layer 262) characterizing the sensor data 220 after having been trained on the context vectors 1180 (generated by the recurrent neural network layer 262) characterizing the training data 240. Artificial neural networks are composed of artificial neurons, which receive input and produce output using an output function (developed and refined by the neural network during the network training). The artificial neurons are arranged in layers (e.g., an input layer, one or more optional hidden layers, and an output layer). Connections provide the output of one neuron and the input to another neuron. Each connection has a weight (also developed and refined by the neural network during the network training) that represents the relative importance of that connection. The fully connected layer 268 is "fully connected," meaning every neuron in one layer has a connection to every neuron in the next layer.

To differentiate between normal and abnormal gaits in the sensor data 220, training data 240 is provided to the neural network 260 that has been coded to indicate whether each piece of training data 240 represents a normal gait or an abnormal gait. Critically, all of the training data 240 captured from a patient that has been diagnosed with a disease that affects the gait is coded as abnormal (even if that patient's gait may appear normal in most instances). The fully connected layer 268 reduces the context vectors 1180 produced by the recurrent neural network layer 262 to an assessment 280 indicating whether the gait of the user gait is normal or abnormal. The assessment 280 may be binary, for example a rating of 1 (indicating a normal gait) or a rating of 0 (indicating an abnormal gait). Alternatively, the fully connected layer 268 may output an assessment 280 representing the probability that the gait of the user is normal or abnormal.

Additionally, the neural network 260 may be trained to identify abnormal gaits indicative of multiple specific diseases. To train the neural network 260 to identify abnormal gaits indicative of multiple specific diseases, training data 240 may be coded to indicate that it was derived from individuals with specific diseases. The neural network 260 is then trained to output an assessment 280 that differentiates between normal and abnormal gaits and distinguishes between the abnormal gaits indicative of different specific diseases.

Additionally, the neural network 260 may be trained to identify abnormal gaits indicative of one or more diseases at differing stages of progression. To train the neural network 260 to identify abnormal gaits indicative of progressive disease(s) at differing stages, training data 240 may be coded to indicate that it was derived from individuals with disease(s) at specific stages of disease progression. The neural network 260 is then trained to output an assessment 280 that differentiates between normal and abnormal gaits and distinguishes between the abnormal gaits indicative of disease(s) at those differing stages of disease progression.

In addition to an assessment 280 of the user's gait based on the sensor data 220 in its entirety, the gait analysis system 200 may generate assessments 530 for each window of the sensor data 220. Referring back to FIG. 5, those gait window assessments 530 may be output to a clinician to provide a granular view of the normality of the user's gait as the user takes individual steps. As shown in FIG. 5, a clinician may view left foot pressure data 310, right foot pressure data 420, and the assessments 530 determined by the gait analysis system 200. In the example shown in FIG. 5, the assessments 530 generated by the gait analysis system 200 indicate instability in areas 532, 534, 536, and 538.

This disclosure describes a neural network 260 with two layers (the recurrent neural network layer 262 and the fully connected layer 268) and an optional attention layer 264. However, as one of ordinary skill in the art will recognize, any of the neural network layers may be a multi-layer neural network. For example, the recurrent neural network layer 262 may use one or more layers wherein the output of the previous recurrent neural network layer is fed to one or more recurrent neural network nodes in the next recurrent neural network layer.) Regarding the fully connected layer 268, multi-layer neural networks are able to differentiate between input data with more and more precision. However, because every piece of data characterizing an individual gait is unique, a multi-layer fully connected layer 268 may produce a model that is "overfit" for this particular purpose. In other words, insignificant variations in user gaits may cause a multi-layer neural network to characterize those user gaits as abnormal. Accordingly, in a preferred embodiment, the fully connected layer 268 is a single layer neural network.

The attention layer 264 is an optional feature that reduces the time necessary to train the neural network 260 to distinguish between normal and abnormal gaits. In embodiments without the attention layer 264, the fully connected layer 268 may generate the assessment 280 based on the final context vector 1180, which describes the final data point 1120 and all of the previously analyzed data points (or, if the recurrent neural network layer 262 is bidirectional, a combination of the final context vectors 1180 in either direction). Alternatively, the fully connected layer 268 may generate the assessment 280 based on the final context vector 1180 based on a combination of a number of context vectors 1180. In embodiments that include the attention layer 264, however, the fully connected layer 268 generates the assessment 280 based on all of the context vectors 1180 generated by the recurrent neural network layer 262, as weighted by the attention layer 264.

As described above, the neural network 260 may be trained to analyze sensor data 220 from a user—and generate an assessment 280 characterizing the gait of the user—after having been trained using training data 240 from individuals other than the user. Additionally, if the gait analysis system 200 receives sensor data 220 from the same user over time, the gait analysis system 200 can generate an assessment 280 of the changes to the user gait over time. Accordingly, by analyzing sensor data 220 from the same user over time, the gait analysis system may assess the progress of a progressive disease over time or, conversely, monitor the user as the user recovers (e.g., from a stroke). The gait analysis system 200 can then be used to perform trend analysis and project future demise or recovery. Using those derived forecasts, the gait analysis system 200 can forecast the expected duration, degree, and finality of a change in user gait.

Figure 13:
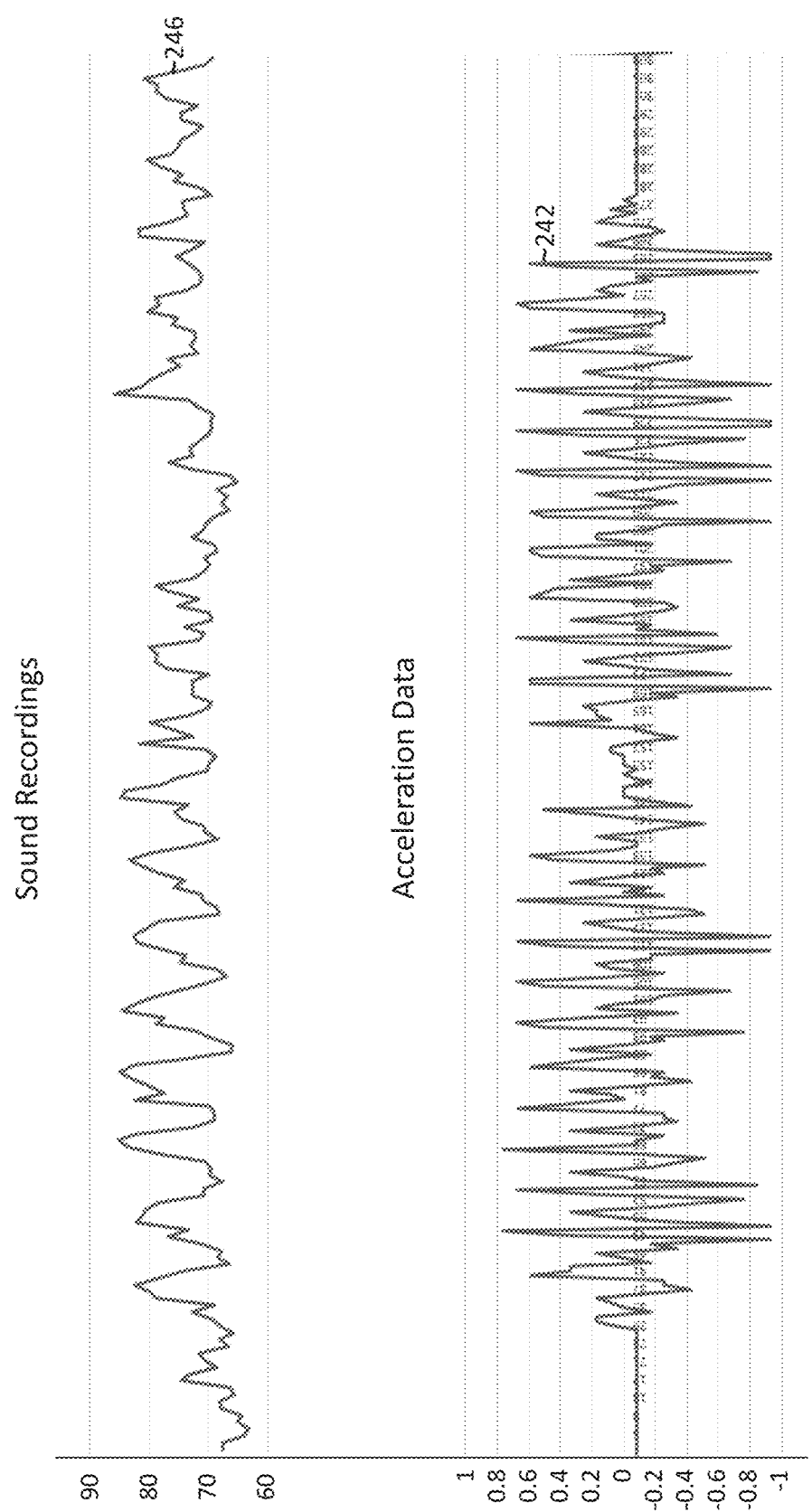
FIG. 13 is a graph of sound recordings and acceleration data captured from a healthy volunteer.
Figure 14:
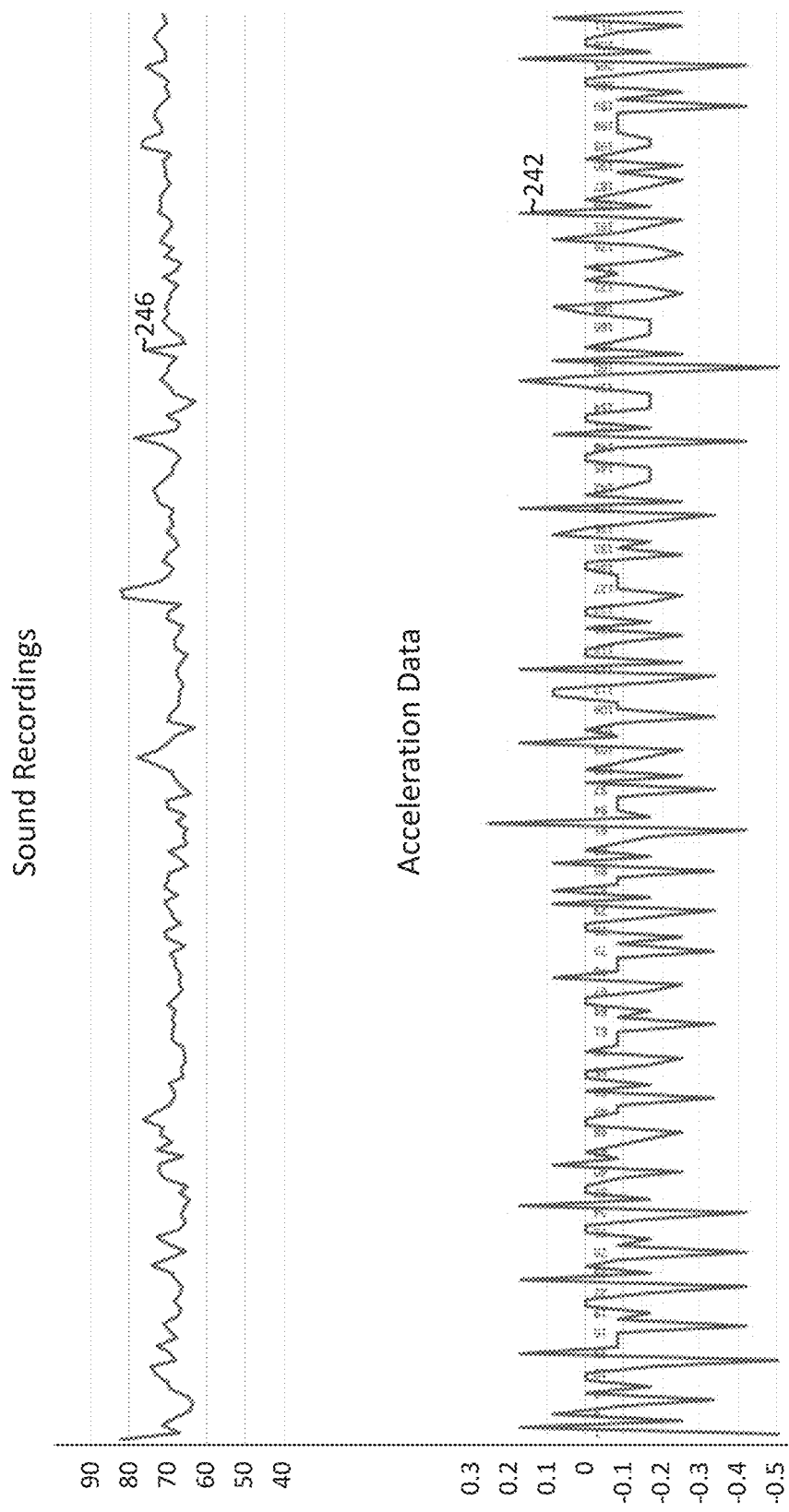
FIG. 14 is a graph of sound recordings and acceleration data captured from a patient that has been diagnosed with Parkinson's disease.
Figure 15:
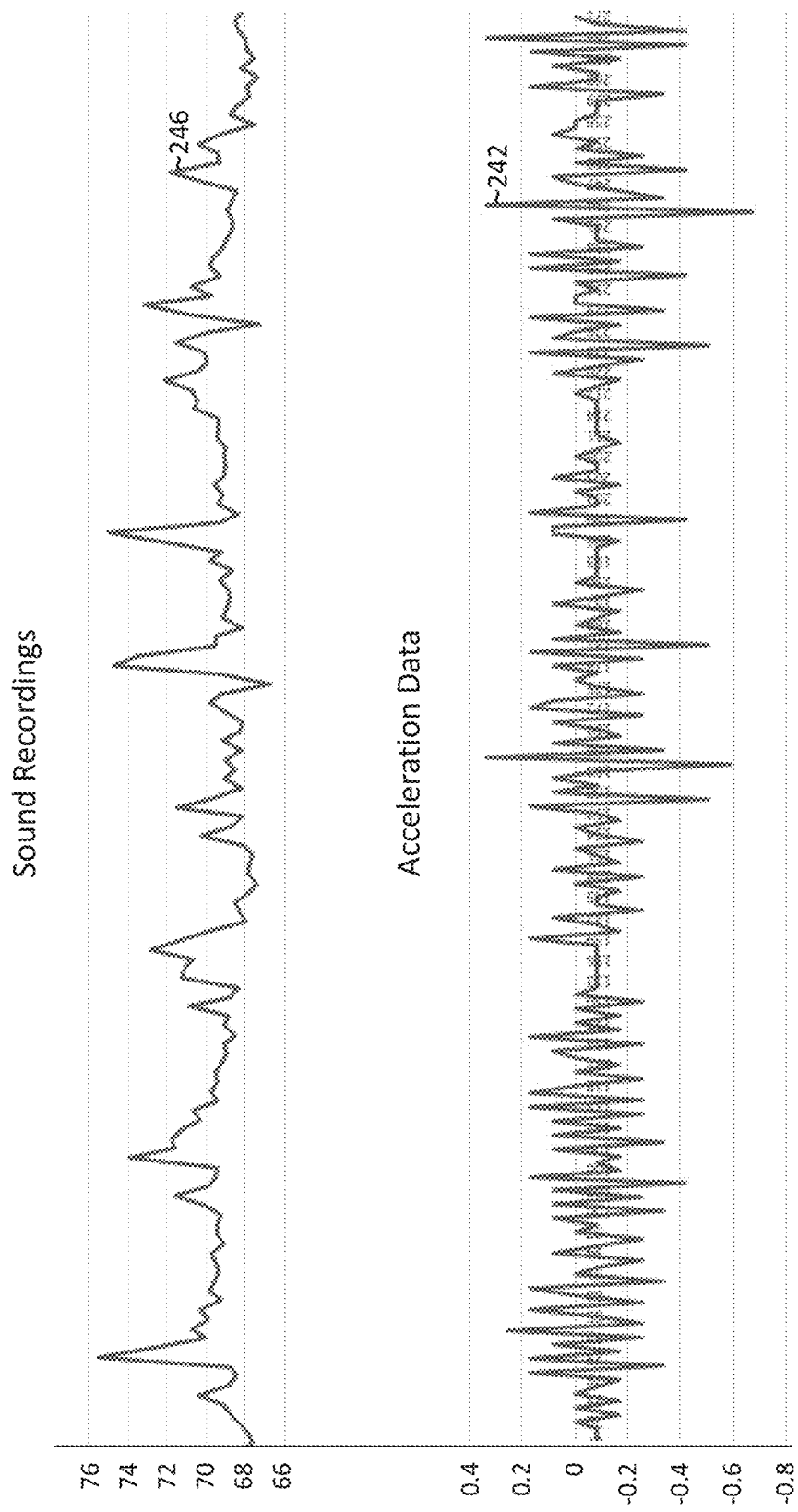
FIG. 15 is a graph of sound recordings and acceleration data captured from a patient with a spastic gait after having suffered a stroke.
Figure 16:
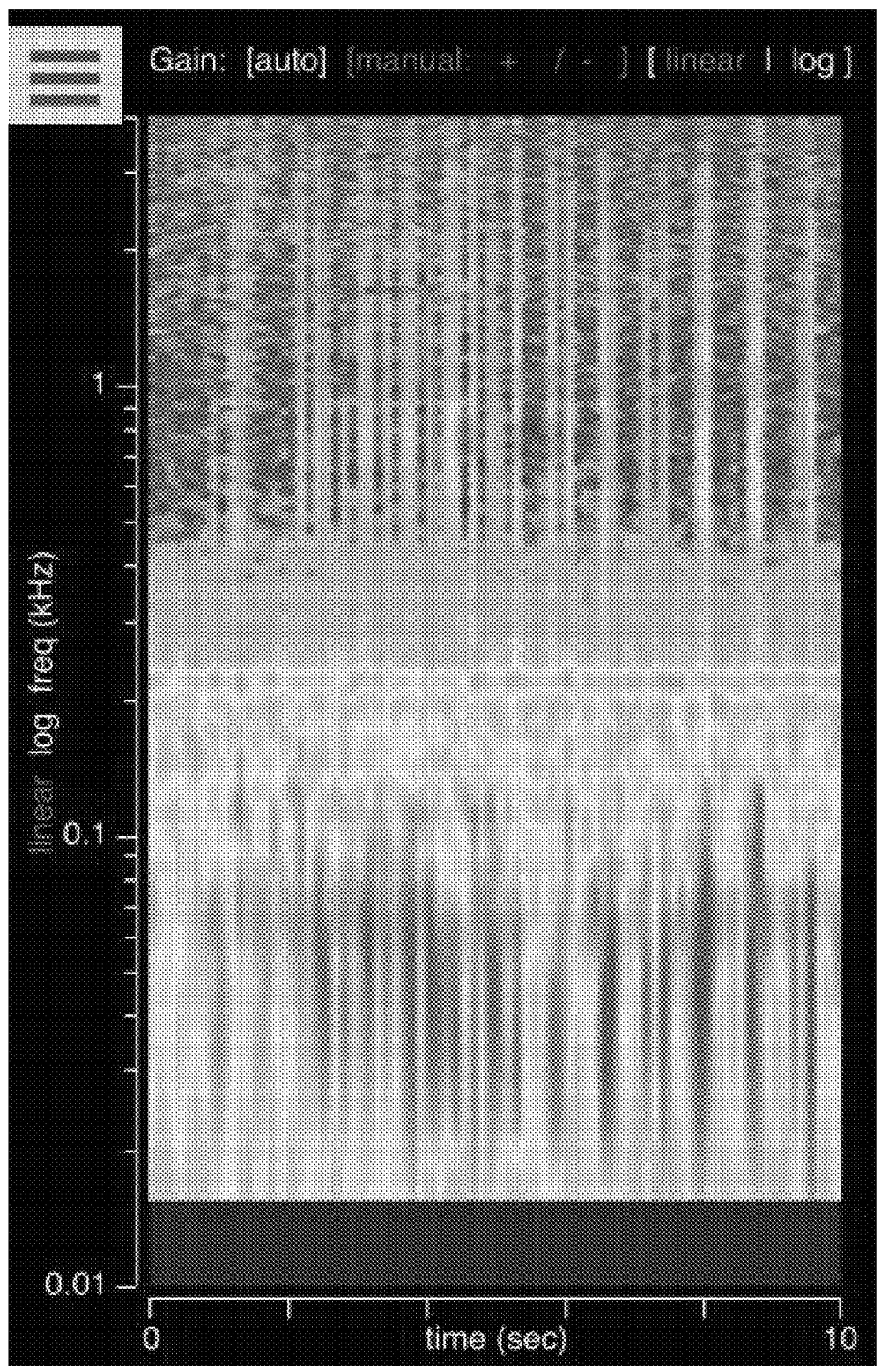
FIG. 16 is a spectrogram of a sound recording captured from a healthy volunteer.
Figure 17:
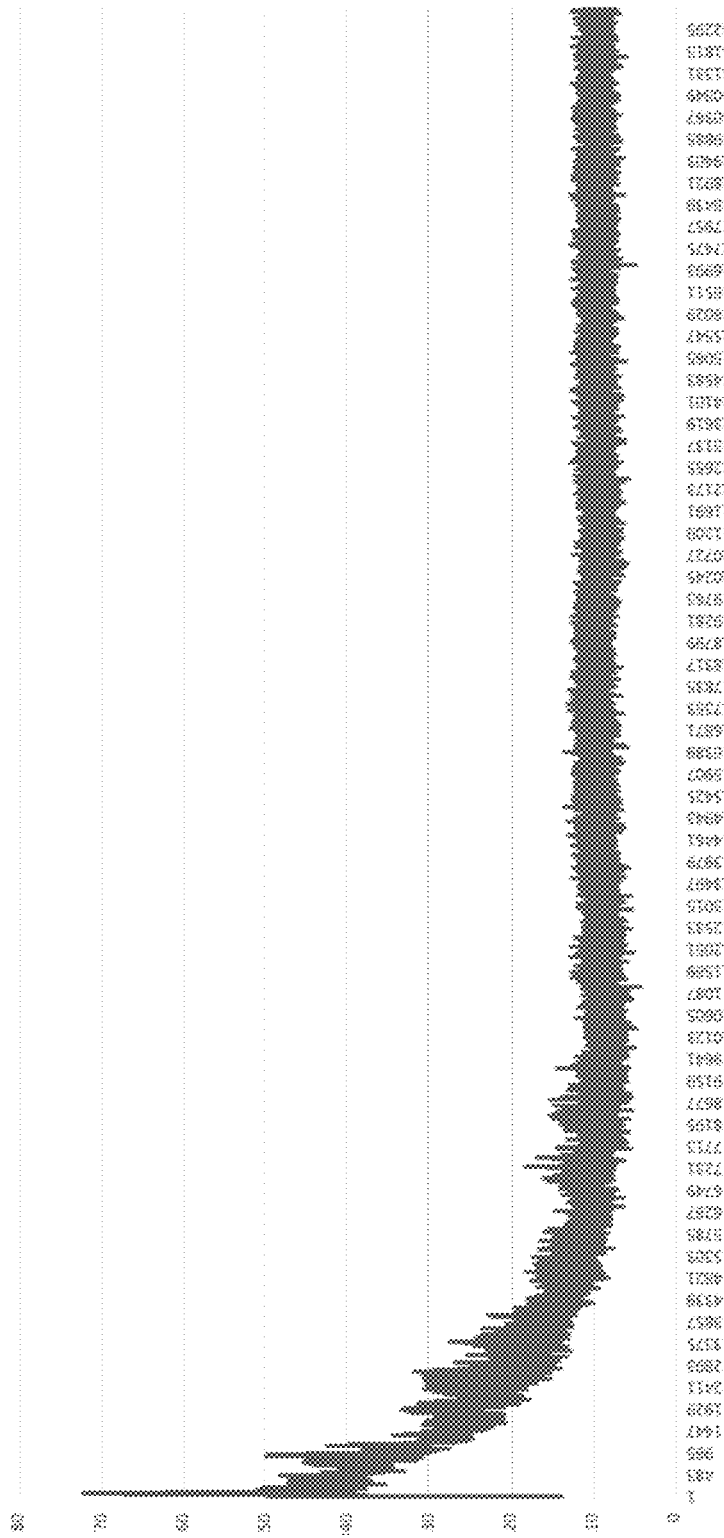
FIG. 17 is another spectrogram of the sound recording shown in FIG. 16.

As described above, training data 240 that includes pressure data 244 may be used to train the neural network 260 to analyze sensor data 220 that includes pressure data 224. However, the same neural network 260 may be used to analyze other types of sensor data 220 (e.g., acceleration data 222, sound recordings 226, spectrograms 227, video recordings 228, etc.) if provided with the same type training data 240 (e.g., acceleration data 242, sound recordings 246, spectrograms 247, video recordings 248, etc.). FIG. 13 is a graph of sound recordings 246 and acceleration data 242 captured from a healthy volunteer. FIG. 14 is a graph of sound recordings 246 and acceleration data 242 captured from a patient that has been diagnosed with Parkinson's disease. FIG. 15 is a graph of sound recordings 246 and acceleration data 242 captured from a patient with a spastic gait after having suffered a stroke. FIGS. 16 and 17 are spectrograms 247 of sound recordings 246 captured from a healthy volunteer.

In some embodiments, the gait analysis system 200 may be trained with different types of training data 240 (e.g., acceleration data 242, pressure data 244, etc.) in parallel, meaning the neural network 260 may be supplied with different types of training data 240 representing the same user gait. If trained in parallel, the neural network 260 will recognize connections between different types of training data 240. Specifically, the recurrent neural network layer 262 will generate the same context vectors 1180 to characterize the same user gait regardless of whether that user gait was identified by acceleration data 242, pressure data 244, etc. Training the neural network 260 in parallel provides many important technical benefits. As a general matter, an assessment 280 generated while analyzing one type of sensor data 220 (e.g., acceleration data 222) is based on training that occurred while analyzing all types of training data 240 (rather than simply acceleration data 242). As a specific matter, the neural network 260 can analyze sensor data 220 from the same user over time—and generate an assessment 280 of the change in gait characteristics—even if different types of user sensor data 220 are available from different time periods.

As described above, the gait analysis system 200 may be trained to recognize gait characteristics associated with certain diseases, such as Parkinson's disease or parkinsonism, peripheral neuropathy, muscle disorders (e.g., ALS, muscular dystrophy, etc.), cerebellar disorders (e.g., stroke, tumor, and degenerative disorders), mood disorders, etc. By analyzing sensor data 220 from the same user over time, the gait analysis system 200 may be used to track the progression of the degenerative diseases as a user's gait deviates farther from normal over time or monitor a patient's recovery (e.g., after a stroke) as the gait of the user approaches normal.

The gait analysis system 200 may also be trained to recognize injuries that affect the gait characteristics of an individual, such as a fall, an injury to a hamstring or muscle, a concussion, other sport injuries, etc. Specifically, the gait analysis system 200 may receive sensor data 220 from the same user over time (e.g., sensor data 220 taken on a run before a practice and sensor data 220 taken on a run after practice). Having been trained with training data 240 from individuals who suffered injuries affecting their gait, the gait analysis system 200 may then recognize whether the user has suffered such an injury in the intervening time period.

As described above, prior art gait analysis methods identify diseases by analyzing a patient's gait characteristics (e.g., strike distance, foot lift, foot pressure, etc.) over a number of steps. However, those methods may be insufficient to identify gait abnormalities that are gradual, episodic, and/or random (such as "freezing of gait"). By generating context vectors 1180 that represent intermediate assessments of the normality of the user gait, the gait analysis system 200 provides important technical and clinical benefits not provided by prior art gait analysis methods. By assessing window-level sensor data 220, the gait analysis system 200 is able to perform event detection and identify gait abnormalities that are gradual, episodic, and/or random. Additionally, the gait analysis system 200 may generate gait window assessments 530 that provide a granular view of the normality of the user's gait as the user takes individual steps.

The foregoing description and drawings should be considered as illustrative only of the principles of the disclosure, which may be configured in a variety of shapes and sizes and is not intended to be limited by the embodiment herein described. Numerous applications of the disclosure will readily occur to those skilled in the art. Therefore, it is not desired to limit the disclosure to the specific examples disclosed or the exact construction and operation shown and described. Rather, all suitable modifications and equivalents may be resorted to, falling within the scope of the disclosure.

What is claimed is:

1. A method, comprising:
   storing gait data comprising;
      training data indicative of abnormal gaits and normal gaits; and
      sensor data indicative of a user gait;
   training a neural network that includes a bidirectional recurrent neural network layer, an attention layer, and a fully connected layer by:
      parsing the training data into a series of training data windows;
      bidirectionally analyzing each training data window in series, by the recurrent neural network layer, to generate two context vectors characterizing each training data window and the previously analyzed training data windows;
      determining, by the attention layer, a relative importance of one of more of the context vectors for distinguishing between training data indicative of normal user gaits and training data indicative of abnormal user gaits;
      weighing one or more of the context vectors, by the attention layer, based on the relative importance of each context vector; and
      training the fully connected layer to distinguish between normal gaits and abnormal gaits based on one or more of the weighted context vectors characterizing the training data;
   parsing the sensor data into a series of sensor data windows;
   bidirectionally analyzing each sensor data window in series, by the recurrent neural network layer, to generate two context vectors characterizing each sensor data window and the previously analyzed sensor data windows, each context vector representing an interim assessment of the normality of the user gait;
   weighing one or more of the context vectors characterizing the sensor data based on a relative importance of each of the one or more context vectors; and
   generating a final assessment characterizing the user gait as normal or abnormal, by the fully connected layer that has been trained using the training data, using one or more of the weighted context vectors characterizing the sensor data.

2. The method of claim 1, wherein analyzing each sensor data window in series comprises:
   analyzing each sensor data window in a forward direction to generate a first context vector characterizing each sensor data window and the previous sensor data windows in the series; and
   analyzing each sensor data window in a backward direction to generate a second context vector characterizing each sensor data window and the subsequent sensor data windows in the series.

3. The method of claim 1, wherein the fully connected layer is a single layer neural network.

4. The method of claim 1, further comprising:
   storing training data indicative of gaits of patients having a plurality of diseases;
   training the fully connected layer to distinguish between the plurality of diseases based on one or more of context vectors characterizing each piece of training data;
   generating a final assessment characterizing the user as indicative of one of the plurality of diseases using one or more of the context vectors characterizing the sensor data.

5. The method of claim 1, further comprising:
   storing training data indicative of patients having a progressive disease at a first stage and the progressive disease at a second stage;
   training the fully connected layer to distinguish between the progressive disease at the first stage and the progressive disease at the second stage based on one or more of context vectors characterizing each piece of training data;

generating a final assessment characterizing the user gait as indicative of the progressive disease at the first stage or the progressive disease at the second stage using one or more of the context vectors characterizing the sensor data.

6. The method of claim 1, further comprising:
storing training data indicative of a gait before an injury and the gait after the injury;
training the fully connected layer to distinguish between the gait before the injury and the gait after the injury;
receiving sensor data indicative of a user gait during a first time period and the user gait during a second time period;
generating a final assessment indicating that the user has suffered the injury between the first time period and the second time period using one or more of the context vectors characterizing the sensor data during the first time period and one or more of the context vectors characterizing the sensor data during the second time period.

7. The method of claim 1, wherein the gait data comprise a plurality of types of gait data.

8. The method of claim 7, wherein the neural network is trained in parallel such that the recurrent neural network layer generates the same context vector to characterize the plurality of types of gait data indicative of the same gait.

9. The method of claim 7, wherein the plurality of types of gait data comprise acceleration data, pressure or force data, sound recordings, spectrograms of sound recordings, or video recordings.

10. A system comprising:
non-transitory computer readable storage media that stores gait data comprising:
training data indicative of abnormal gaits and normal gaits; and
sensor data indicative of a user gait;
a hardware computer processor that:
stores a neural network that includes a bidirectional recurrent neural network layer, an attention layer, and a fully connected layer:
parses the training data into a series of training data windows;
trains the recurrent neural network layer to bidirectionally analyze each training data window in series and generate two context vectors characterizing each training data window and the previously analyzed training data windows;
trains the attention layer to determine a relative importance of one or more of the context vectors for distinguishing between training data indicative of normal user gaits and training data indicative of abnormal user gaits;
weights one or more of the context vectors based on the relative importance of each context vector;
trains the fully connected layer to distinguish between normal gaits and abnormal gaits based on one or more of the weighted context vectors characterizing the training data;
parses the sensor data into a series of sensor data windows;
bidirectionally analyzes each sensor data window in series, by the recurrent neural network layer, to generate two context vectors characterizing each sensor data window and the previously analyzed sensor data windows, each context vector representing an interim assessment of the normality of the user gait;
weighs one or more of the context vectors characterizing the sensor data based on a relative importance of each context vector; and
generates a final assessment characterizing the user gait as normal or abnormal, by the fully connected layer that has been trained using the training data, using one or more weighted context vectors characterizing the sensor data.

11. The system of claim 10, wherein the bidirectional recurrent neural network:
analyzes each sensor data window in a forward direction to generate a first context vector characterizing each sensor data window and the previous sensor data windows; and
analyzes each sensor data window in a backward direction to generate a second context vector characterizing each sensor data window and the subsequent sensor data windows.

12. The system of claim 10, wherein the fully connected layer is a single layer neural network.

13. The system of claim 10, wherein:
the training data comprise data indicative of gaits of patients having a plurality of diseases;
the fully connected layer is trained to distinguish between the plurality of diseases based on one or more of context vectors characterizing each piece of training data;
the final assessment characterizes the user gait as indicative of one of the plurality of diseases using one or more of the context vectors characterizing the sensor data.

14. The system of claim 10, wherein:
the training data is indicative of patients having a progressive disease at a first stage and the progressive disease at a second stage;
the fully connected layer is trained to distinguish between the progressive disease at the first stage and the progressive disease at the second stage based on one or more of context vectors characterizing each piece of training data;
the fully connected layer is configured to generate a final assessment characterizing the user gait as indicative of the progressive disease at the first stage or the progressive disease at the second stage using one or more of the context vectors characterizing the sensor data.

15. The system of claim 10, wherein:
the training data comprise data indicative of a gait before an injury and the gait after the injury;
the fully connected layer is trained to distinguish between the gait before the injury and the gait after the injury;
the sensor data is indicative of a user gait during a first time period and the user gait during a second time period;
the fully connected layer is configured to generate a final assessment indicating that the user has suffered the injury between the first time period and the second time period using one or more of the context vectors characterizing the sensor data during the first time period and one or more of the context vectors characterizing the sensor data during the second time period.

16. The system of claim 10, wherein the gait data comprise a plurality of types of training data.

17. The system of claim 16, wherein the neural network is trained in parallel such that the recurrent neural network layer generates the same context vector to characterize the plurality of types of gait data indicative of the same gait.

18. The system of claim 16, wherein the plurality of types of gait data comprise acceleration data, pressure or force data, sound recordings, spectrograms of sound recordings, or video recordings.

* * * * *